(12) United States Patent
Cota et al.

(10) Patent No.: US 9,180,262 B2
(45) Date of Patent: Nov. 10, 2015

(54) DELIVERY OF NEBULIZED MEDICINES

(71) Applicants: Sarah Cota, Bend, OR (US); Mathew S. Smith, Bend, OR (US)

(72) Inventors: Sarah Cota, Bend, OR (US); Mathew S. Smith, Bend, OR (US)

(73) Assignee: JETTSTREAM, INC., Bend, OR (US)

( * ) Notice: Subject to any disclaimer, the term of this patent is extended or adjusted under 35 U.S.C. 154(b) by 463 days.

(21) Appl. No.: 13/663,861

(22) Filed: Oct. 30, 2012

(65) Prior Publication Data

US 2013/0306060 A1 Nov. 21, 2013

Related U.S. Application Data

(60) Provisional application No. 61/647,084, filed on May 15, 2012.

(51) Int. Cl.
*A61M 11/00* (2006.01)
*A61M 15/00* (2006.01)
(Continued)

(52) U.S. Cl.
CPC ............ *A61M 11/00* (2013.01); *A61B 19/5202* (2013.01); *A61M 15/00* (2013.01); *A61M 16/08* (2013.01); *A61M 16/0875* (2013.01); *F21S 6/006* (2013.01); *F21V 21/26* (2013.01); *F21V 21/28* (2013.01); *F21V 21/32* (2013.01); *F21V 33/0068* (2013.01); *A61M 11/06* (2013.01); *A61M 2205/586* (2013.01); *A61M 2205/587* (2013.01); *A61M 2209/08* (2013.01); *A61M 2209/082* (2013.01); *A61M 2210/0618* (2013.01); *A61M 2210/0625* (2013.01)

(58) Field of Classification Search
CPC ..... A61M 11/00; A61M 11/02; A61M 16/14; A61M 16/0875; A61M 15/00; A61M 2205/587; A61M 2209/082; A61M 2205/586; A61M 2210/0618; A61M 2210/0625; A61M 11/06; A61M 16/08; A61M 2209/08; F21V 33/0068; F21V 21/26; F21V 21/28; F21V 21/32; F21S 6/006; A61B 19/5202
USPC .................. 128/200.14, 845, 202.27, 204.18, 128/205.13, 846, 207.11
See application file for complete search history.

(56) References Cited

U.S. PATENT DOCUMENTS

| 1,571,959 A | 2/1926 | Adele |
| 2,419,860 A | 4/1947 | Urrutia |

(Continued)

FOREIGN PATENT DOCUMENTS

| WO | 9927818 | 6/1999 |
| WO | 2005112555 | 12/2005 |
| WO | 2007021969 | 2/2007 |

OTHER PUBLICATIONS

PCT Search Report and Witten Opinion, PCT/US2013/039324, dated Sep. 19, 2013, 16 pages.

(Continued)

*Primary Examiner* — Steven Douglas
(74) *Attorney, Agent, or Firm* — Leber Patent Law P.C.

(57) ABSTRACT

Devices are disclosed that include a positionable elongated member configured to support and delivery tube and maintain a distal end of the tube in a desired position, and to allow the position of the distal end of the tube to be adjusted by a user, and an attachment device configured to allow a proximal end of the elongated member to be secured in a fixed position. These devices may be used, for example, in the delivery of vaporized medicine to a patient, e.g., a child or infant on a bed.

22 Claims, 4 Drawing Sheets

(51) Int. Cl.
- *A61M 16/08* (2006.01)
- *F21V 33/00* (2006.01)
- *F21S 6/00* (2006.01)
- *F21V 21/26* (2006.01)
- *F21V 21/28* (2006.01)
- *F21V 21/32* (2006.01)
- *A61B 19/00* (2006.01)
- *A61M 11/06* (2006.01)

(56) References Cited

U.S. PATENT DOCUMENTS

| | | | |
|---|---|---|---|
| 2,963,247 A | 12/1960 | Collier | |
| 3,221,733 A | 12/1965 | Beasley | |
| 3,931,452 A | 1/1976 | Nilsson | |
| 3,971,538 A | 7/1976 | Marvich | |
| 4,020,834 A | 5/1977 | Bird | |
| 4,282,869 A | 8/1981 | Zidulka | |
| 4,321,917 A | 3/1982 | Campbell | |
| 4,338,924 A | 7/1982 | Bloom | |
| 4,554,916 A | 11/1985 | Watt | |
| 4,568,027 A * | 2/1986 | Lazarus | 239/590.3 |
| 4,593,688 A | 6/1986 | Payton | |
| 4,595,008 A | 6/1986 | Guibert | |
| 4,646,750 A | 3/1987 | Williams | |
| 4,679,551 A | 7/1987 | Anthony | |
| 4,732,147 A | 3/1988 | Fuller | |
| 4,863,133 A | 9/1989 | Bonnell | |
| 5,014,693 A | 5/1991 | Sauberli et al. | |
| 5,357,945 A | 10/1994 | Messina | |
| 5,470,037 A * | 11/1995 | Willis | 248/125.9 |
| 5,636,627 A | 6/1997 | Rochester | |
| 5,692,494 A | 12/1997 | Pernetti | |
| 5,941,839 A | 8/1999 | Ishikawa | |
| 6,065,473 A | 5/2000 | McCombs et al. | |
| 6,224,027 B1 | 5/2001 | Johnson et al. | |
| 6,308,707 B1 | 10/2001 | Lu | |
| 6,371,115 B1 | 4/2002 | Cewers et al. | |
| 6,450,166 B1 | 9/2002 | Lavimodiere et al. | |
| 6,619,288 B2 | 9/2003 | Demers et al. | |
| 6,837,238 B2 | 1/2005 | McDonald | |
| 7,004,437 B2 | 2/2006 | Bauer et al. | |
| 7,036,502 B2 | 5/2006 | Manne | |
| 7,040,581 B2 | 5/2006 | Noelke et al. | |
| 7,063,765 B2 | 6/2006 | Kudo et al. | |
| 7,089,941 B2 | 8/2006 | Bordewick et al. | |
| 7,124,755 B2 | 10/2006 | Van Hooser | |
| 7,267,305 B2 | 9/2007 | Kreuzer et al. | |
| 7,351,231 B2 * | 4/2008 | Young | 604/264 |
| 7,357,136 B2 | 4/2008 | Andrews et al. | |
| 7,453,585 B2 | 11/2008 | Dodge et al. | |
| 7,597,298 B2 | 10/2009 | Papendieck et al. | |
| 7,694,680 B2 | 4/2010 | Brichetto | |
| 7,744,043 B2 | 6/2010 | Otinger | |
| 7,975,693 B2 | 7/2011 | Geiselhart et al. | |
| 8,011,071 B2 | 9/2011 | O'Brien | |
| 8,181,918 B2 | 5/2012 | McCloud | |
| 8,282,050 B2 | 10/2012 | Georgey | |
| 8,360,058 B2 | 1/2013 | Ahearn | |
| 8,534,618 B2 | 9/2013 | Mays | |
| 8,540,196 B1 | 9/2013 | Hodson | |
| 8,794,233 B2 | 8/2014 | Ahearn et al. | |
| 2002/0074463 A1 | 6/2002 | Nakamura | |
| 2003/0116167 A1 | 6/2003 | Van Hooser | |
| 2007/0045481 A1 | 3/2007 | Adams | |
| 2007/0295869 A1 | 12/2007 | Noelke et al. | |
| 2008/0078397 A1 | 4/2008 | Christianson et al. | |
| 2008/0185359 A1 | 8/2008 | Baxter | |
| 2009/0039210 A1 | 2/2009 | Shrivastava et al. | |
| 2009/0065005 A1 | 3/2009 | Ades | |
| 2009/0179117 A1 | 7/2009 | Thomas | |
| 2013/0174838 A1 | 7/2013 | Youngblood | |
| 2013/0306060 A1 | 11/2013 | Cota et al. | |

OTHER PUBLICATIONS

Cumulus, Modern Ultrasonic Nebulizer, Heyer Medical AG, Nov. 2006.
Kid O's Bear, #EO-KBN-4300, Mercury Medical, p. 270, commercially available at least as early as Aug. 2011.
OxyPhone, The Nebulizer Phone for Children, www.oxyphone.com; commercially available at least as early as May, 2008.
Ari, Arzu, "Jet, Ultrasonic, and Mesh Nebulizers: An Evaluation of Nebulizers for Better Clinical Outcomes", Eurasian Journal of Pulmonology 2014; 16:1-7.

\* cited by examiner

DELIVERY OF NEBULIZED MEDICINES

CROSS-REFERENCE TO RELATED APPLICATION

This patent application claims priority to U.S. Provisional Application No. 61/647,084, which was filed on May 15, 2012. The entirety of this application is incorporated herein by reference.

BACKGROUND

Many respiratory diseases, including asthma, are treated with the use of a device called a nebulizer. These "nebulizers" take liquid or solid medication (such as respiratory steroids) and, through compressed air or other technologies, nebulize the medication into a fine mist that is then blown through a tube into a mask. Generally, the following conditions must be met during delivery of the nebulized medicine: a) the mask must be placed on a cooperative patient's mouth and nose, b) the patient must sit in an upright position, c) the mask must form a tight seal on the patient's face, and d) the medicine must be administered for a fairly extended period, e.g., 10 minutes, with the patient in this state. During this process (a)-(d) are often not possible, and the patient may be uncooperative during the treatment resulting in an incomplete or ineffective treatment. If treatments are not given effectively on a regular basis the result is often deterioration of the respiratory condition, often resulting in an attack that sends the patient to the Hospital or Emergency Room.

Research has identified that treatments given at night while the subject is sleeping are most effective due to the deep regular breathing conditions achieved during sleep. Medication delivered to a sleeping subject penetrates deeper into the lungs, allowing more effective treatment and prevention of respiratory attacks. However, when delivering treatments to a sleeping patient, parents or caregivers are often forced to manipulate nebulizer devices or use them ineffectively.

In hospital settings where multiple infants, or patients have respiratory conditions that require nebulized medical treatments, nurses and care givers are required to administer treatments on an individual basis. Due to current limitations in respirator medical devices, nurses and caregivers generally must physically hold a mask on or near a patient's face and carefully watch that the medicine cup is held in an upright orientation.

SUMMARY

Generally, this invention relates to devices and methods for delivery of a nebulized medicine to a patient. The devices disclosed herein may be configured for use in environments such as patients' homes, hospitals, doctors' offices, and nursing homes.

In some embodiments, the devices are configured so that the patient may remain in his or her current location, positioning, and state (e.g., sitting in a chair or lying down, either asleep or awake) and the device can be transported and positioned in such a manner as not to disrupt or seriously change the patient's current state, minimizing the likelihood of sending the patient into an uncooperative state where treatments are less effective. In some cases, the devices can be used hands-free by suspending a portion of the device in a position to effectively deliver medication in close proximity to the nose and mouth of the patient without touching the patient. In preferred implementations, unlike mask delivery or intubation, delivery using the devices disclosed herein is substantially "contact-free," without a mask or other portion of the device contacting the patient's nose or mouth.

In some implementations, the devices are used for delivery of nebulized medicines to infants in a hands-free manner, allowing nurses to administer treatments to multiple infants at one time.

In one aspect, the invention features a device that includes a positionable elongated member configured to support a delivery tube and maintain a distal end of the tube in a desired position, and to allow the position of the distal end of the tube to be adjusted by a user (e.g., a patient, caregiver, or clinician); and an attachment device configured to allow a proximal end of the elongated member to be supported in a fixed position.

Some implementations may include one or more of the following features.

The positionable elongated member may include an articulated arm assembly, which may, for example, comprise two or more, in some cases three or more, pivotably connected arm segments. Alternatively, or in addition, the positionable elongated member may include a positionable tubular member, e.g., a continuously positionable metal tube such as gooseneck tubing or the like.

The positionable elongated member may include or contain a light or lamp (not shown) configured to allow the user to illuminate a treatment area, e.g., the patient's face. Moreover, a nozzle may be disposed at a distal end of the positionable elongated member. The nozzle is configured to deliver a spray of liquid mist, or nebulized medicament from the delivery tube, and may in some cases be configured to allow a user to adjust a spray pattern of the vaporized medicament. In some cases, the light or lamp is disposed in or adjacent to the nozzle. The nozzle may be positionably attached to the distal end of the positionable elongated member, e.g., by a ball joint that defines a lumen.

In some cases, the device further includes a medicine cup, or nebulizer mounted on the positionable elongated member in fluid communication with the delivery tube during use of the apparatus. The medicine cup may be mounted so that the axis of the medicine cup will remain substantially vertical during use of the apparatus.

In some cases, the device further includes the delivery tube, which may be disposable. When the device is used in a hospital or other clinical setting the delivery tube is generally disposable after a single use, whereas in a home setting the tube may be used for multiple uses prior to replacement.

The attachment device may comprise a flat base, e.g., configured to slip under a mattress or pillow, and/or to rest flat on a floor or table. In other embodiments, the attachment device may comprise a wall mount or clamp, e.g., a clamp configured to mount on a headboard of a bed. In some cases, the attachment device may be interchangeable, e.g., between a flat base, a wall mount, and a clamp. In some cases, the proximal end is coupled to the attachment device so as to allow rotational or pivoting motion of the proximal end.

The invention also features methods of delivering nebulized medicines. In one aspect, the invention features a method that includes delivering a spray of nebulized medicine to a patient, without the use of a mask, by positioning the distal end of a delivery tube adjacent the face of the patient using a positionable elongated member configured to support the delivery tube in a desired position relative to the patient.

Some implementations include one or more of the following features.

The method may further include, prior to the delivering step, adding a supply of the medicine, in liquid form, to a medicine cup mounted on the elongated member.

In some cases, the patient may be lying down, either sleeping or awake. The patient may be an infant, a small child, or an adult. The medicine may, for example, be an asthma medicine.

An adjustable nozzle may be mounted at the distal end of the delivery tube and the method may further include adjusting a spray pattern of the nebulized medicine using the adjustable nozzle.

The method may further include directing a light that is associated with the positionable elongated member to shine on the face of the patient during treatment. This light may also be used to indicate position and/or distance relative to the patient's nose and mouth. For example, in some implementations as the nozzle moves out of position the light will fade or move off target. The light may thus be used to aid in the proper positioning of the distal end of the device. In some implementations, the light is configured so that light intensity will increase/decrease proportionately with changes in the mist delivery/density with respect to the patient's nose and mouth.

The method may further include, during delivery of the spray to the patient, delivering a spray of nebulized medicine to a second patient, without the use of a mask, by positioning the distal end of a second delivery tube adjacent the face of the second patient using a positionable elongated member configured to support the delivery tube in a desired position relative to the second patient. In this manner, several patients, e.g., several children in the same family in a home setting, or several infants in the same ward in a hospital setting, may be given treatment simultaneously.

The description may use perspective-based descriptions such as up/down, back/front, and top/bottom. Such descriptions are merely used to facilitate the discussion and are not intended to restrict the application of the embodiments of the present invention.

As used herein, the term "compressor" refers to any device that compresses air, for example an electrically powered unit, which may be powdered, e.g., by direct wall alternating current (AC volts), or direct current (DC volts) by means of either battery voltage or an AC volts to DC volts converter. The compressor is understood to take in atmospheric air and compress it to some output magnitude greater than atmospheric pressure.

As used herein, the term "vaporizer" is used to describe an apparatus that transforms drugs into small fine particles that are necessarily lighter than their bulk solid or liquid form and thus can be conveyed in a partially suspended state by means of an air current. The device is not limited to a particular method, manufacturer, or technology. A vaporizer described in this invention is not necessarily dependent on the compressor and can operate independent of a compressor, eliminating the compressor from the system.

As used herein, the term "nebulizer" refers to the entire system of creating small partially suspended medication conveyed by air current. This could contain, but is not limited to, a compressor and vaporizer cup, or just a vaporizer, as well as any other technology that creates and conveys treatments through air to be inhaled by patients.

As used herein, the terms "nebulized medication," "nebulized drugs", "vaporized medicine," and variants of these terms, refer to the product output by the nebulizer where particles of medication or drugs are partially suspended in an air medium.

As used herein, the term "tubing" is used to describe a hollow flexible apparatus used to convey either air or air and vaporized medication between locations within the device, or between different devices within the system.

As used herein, the term "nozzle" refers to the final exit point of nebulized medication, at which the nebulized medicine is conveyed to the patient to be inhaled.

As used herein, the terms "articulating," "articulation" and their derivatives, describe two parts that are coupled in a manner that allows relative rotational, radial, or translational motion of two or more components of the device.

In the following detailed description, reference is made to the accompanying drawings in which are shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

DETAILED DESCRIPTION

Figure 1:
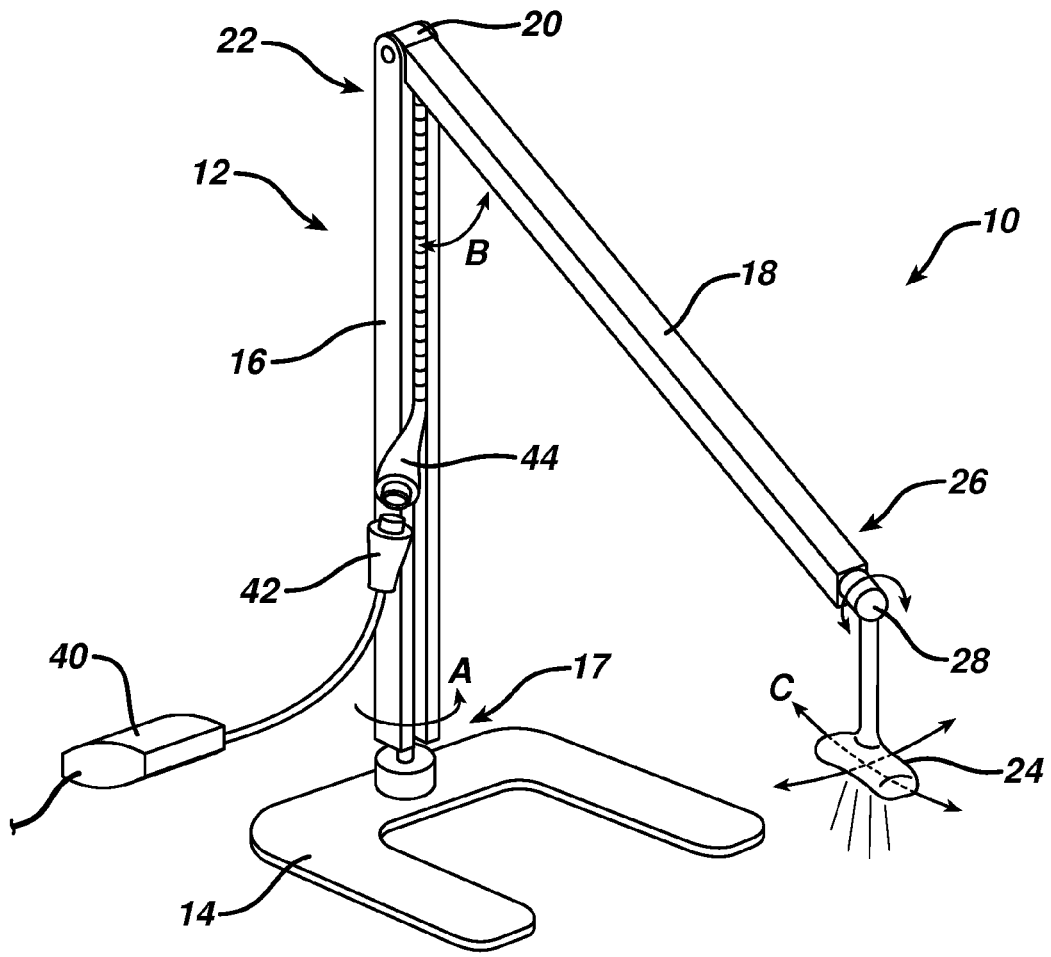
FIG. 1 is a perspective view of a device according to one embodiment, in which the device includes an articulated arm.
Figure 1A:
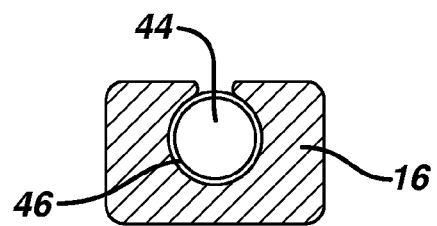
FIG. 1A is a cross-sectional view of an arm of the device shown in FIG. 1 with a delivery tube in place.

Referring to FIG. 1, in one embodiment a nebulized medicine delivery device 10 includes a positionable elongated member 12 supported by a base 14. In the embodiment shown in FIG. 1, the positionable elongated member 12 includes a first arm 16 which is coupled to the base 14 at its proximal end 17, and positionably coupled to a second arm 18 by an articulating hinge 20 at its distal end 22. As indicated by arrow A, the proximal end 17 of the first arm is preferably mounted on the base 14 so that it can rotate, and in some cases pivot, with respect to the base to enhance the overall positionability of the device. It is generally preferred that movement be limited to rotation, as indicated by arrow A, so that the first arm 16 remains generally vertical. While rotation is preferred, if desired the first arm can be fixedly mounted to the base. The articulating hinge 20 allows the first arm 16 and second arm 18 to pivot about the axis of the hinge in the manner indicated by arrow B, The device 10 also includes a compressor 40 which delivers compressed gas (e.g., air) to a medicine cup 42 which, when the device is in use, contains a supply of medicine. The medicine cup 42 is connected to the first arm 16 so as to hold the medicine cup in a stable, substantially vertical position during delivery of the medicine to enhance the effectiveness of the vaporizer. The compressor is connected to a power supply (not shown). Medicine is nebulized in the medicine cup and then delivered to the patient via a delivery tube 44. As shown in detail in FIG. 1A, the delivery tube 44 is disposed in a channel 46 in the first arm 16. The second arm 18 includes a similar channel (not shown). These channels allow the tube to be held securely but removable within the positionable elongated member 12. Because the delivery tube is removable from the channel it can be easily replaced.

A nozzle 24 is mounted at the distal end 26 of the second arm, for delivery of the vaporized medicine to an area adjacent the patient's face. Mounting is preferably by a pivotable connection, e.g., a ball joint 28, as shown, to provide fluid communication between the nozzle 24 and the delivery tube 44 while allowing the position of the nozzle to be finely adjusted as indicated by arrows C. An example of a suitable structure for the ball joint is shown in detail in FIG. 4.

Figure 4:
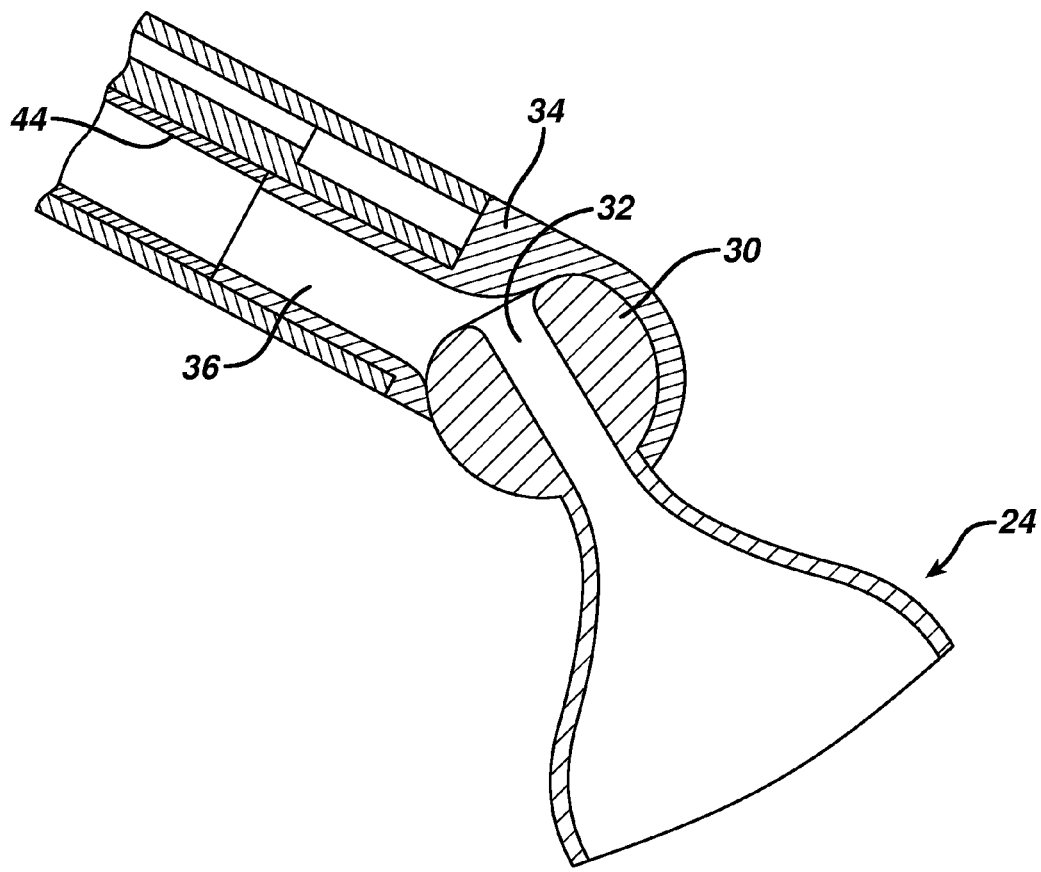
FIG. 4 is a cross-sectional view of a ball joint that may be used to connect the nozzle to the articulated arm in the device shown in FIG. 1.

As shown in FIG. 4, the ball joint includes a ball 30 that defines a lumen 32 and a socket 34 that receives the ball 30 and defines a lumen 36 that is in fluid communication with lumen 32 in all rotational positions of the ball. Together, the lumens 32 and 36 communicate with the lumen defined by the delivery tube 44, allowing delivery of the vaporized medication through the ball joint to the nozzle. The ball may be integral with the nozzle, as shown, or may be separate from the nozzle and attached to the nozzle, e.g., by a snap fit or other engagement. The ball joint allows the position of the nozzle to be continuously adjustable in both an angular and rotational axis to create positioning in a full hemispherical attitude. The nozzle and ball joint may be replaceable, along with the delivery tube, or may be sterilizable.

In use, the base 14 may be positioned on the floor or in any desired location, and the positionable elongated member 12 used to position the nozzle in various locations in space so that the nozzle 24 is generally adjacent to the patient's face. The orientation of the nozzle 24 can then be finely adjusted to the patient's face through the motion of the rotating ball joint. Once the position of the device has been adjusted in this manner, the device can be used hands-free, with the user needing only to monitor the patient and readjust the position of the nozzle if the patient moves out of position relative to the nozzle.

While the device shown in FIG. 1 has only two arms, a third arm, or multiple articulated arms, could be interposed between the second arm and the nozzle if desired, to provide further articulation. In this case, the axes of rotation of the various hinges between the arms may be oriented differently. For example, if a third arm (not shown) were interposed between the second arm 18 and the nozzle 24, the hinge connecting the second and third arms could have an axis of rotation perpendicular to that of the hinge 20 that connects the first arm 16 to the second arm 18 in FIG. 1. If desired any of the joints could be replaced by ball joints to provide 2 axes of freedom and accommodate a broader range of motion.

If desired, the nozzle 24 may be omitted and the vaporized medicine simply delivered from the end of the delivery tube, or a different type of nozzle may be used, e.g., a spray head (not shown) which may be adjustable, e.g., in the manner of an adjustable garden hose sprayer.

FIG. 1 includes arrows depicting degrees of freedom and axes of motion that may be favorable in this particular embodiment; however additional, fewer, or different motions may be incorporated in other embodiments.

Figure 2:
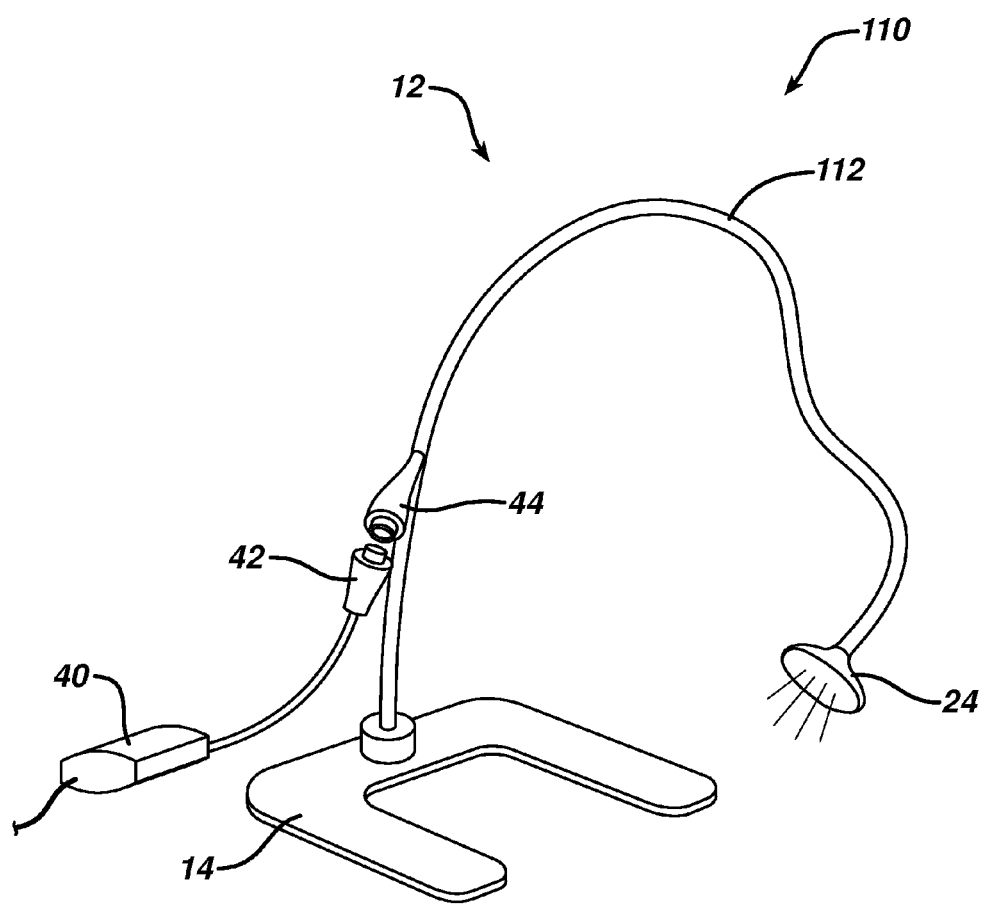
FIG. 2 is a perspective view of a device according to an alternate embodiment, in which the device includes a continuously flexible arm.

FIG. 2 depicts an alternative device 110, in which the articulating arms shown in FIG. 1 are replaced by one continuous flexible member 112. This flexible member needs to be sufficiently rigid so as to maintain the delivery tube in a desired position, without support by the user, during use of the device, while being sufficiently flexible so as to allow the user to easily position and reposition the distal end of the flexible member without having to exert undue effort. One suitable type of flexible member is the flexible, multisegmented tubing referred to as "gooseneck tubing." Other types of positionable metal or plastic tubing may also be used.

As discussed above with regard to FIG. 1, the flexible member 112 is mounted at one end on a base 14. In this case, due to the continuous flexibility of member 112, mounting is generally fixed, though rotatable mounting (as shown in FIG. 1) may be used if desired. The flexible member may be hollow, so that the delivery tube 44 may be routed through the flexible member 112, as shown, or may be solid, in which case the delivery tube is secured, e.g., clipped, to the flexible member 112 at various points along its length (not shown.) A nozzle 24 and vaporizer 42 are mounted on the flexible member 112 as in the embodiment shown in FIG. 1. Due to the continuous flexibility of member 112 the ball joint connection between the member 112 and the nozzle 24 may in some cases be omitted. However, a ball joint (not shown) may be provided if fine adjustability of the nozzle relative to the patient's face is desired.

During use, the nozzle 24 may be adjusted to any position within the reach of the flexible member 112. It is generally preferred that the flexible member 112 not be extended so far horizontally that its proximal portion, where the medicine cup is mounted, ceases to be generally vertical. To prevent this overextension, in some cases a proximal portion of the member 112, between the base and medicine cup, may be rigid or less flexible than the remainder of the member 112.

Figure 3:
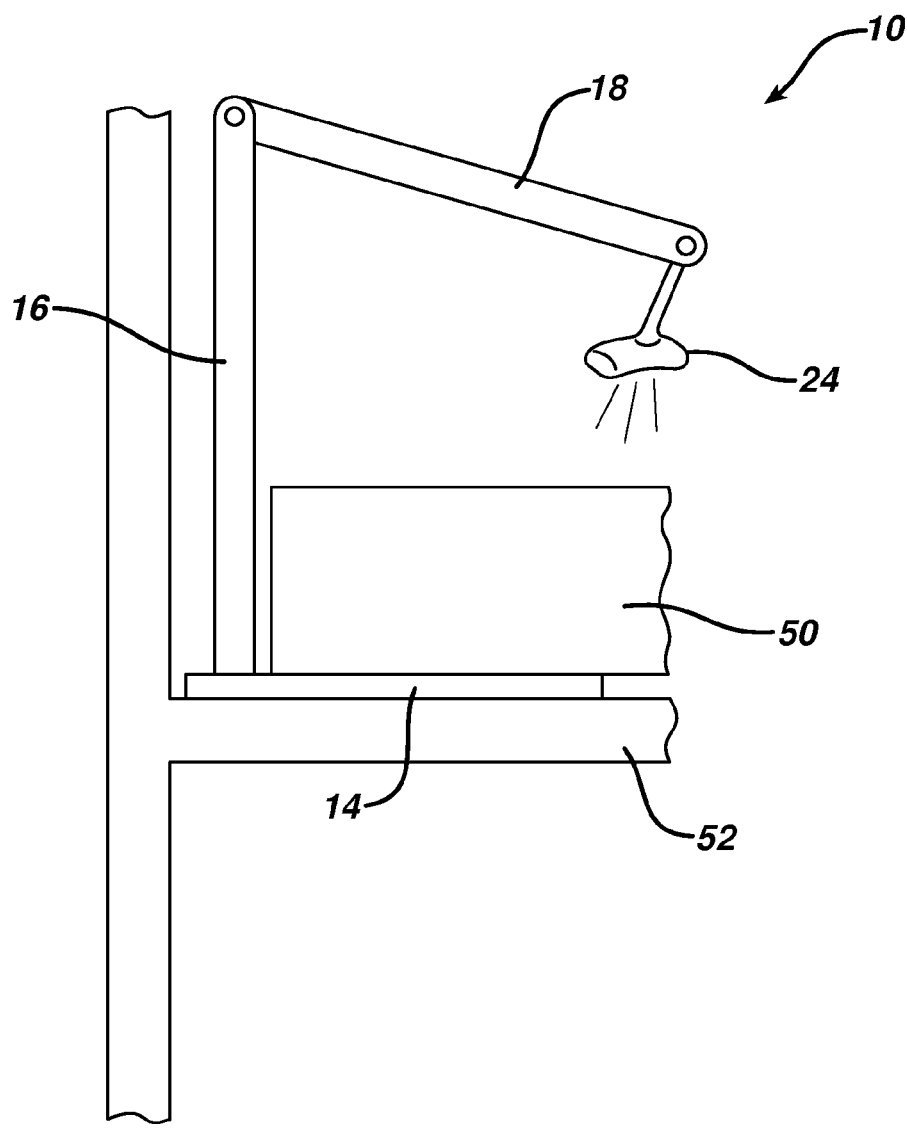
FIG. 3 is a side plan view of the device shown in FIG. 1, showing the device positioned for use with its base fixed under a mattress.

As shown in FIG. 3, in some embodiments the base 14 of device 10 can be configured to be placed under a mattress or pillow 50 and the second arm 18 can suspend over a bed 52, allowing the nozzle to be positioned in close proximity to a sleeping patient's nose and mouth. Alternatively, the base 14 may be configured to be attached directly to a hospital bed frame to accommodate patients within the clinical or hospital system. In other embodiments, the device may be clamped to the bed, e.g., to a headboard, bedframe, or to another object such as a table or vertical stand, or may have a base that will sit flat on the floor. While the arrangement shown in FIG. 3 utilizes the articulated device shown in FIG. 1, the continuously flexible device shown in FIG. 2 may be used in a similar manner.

Other Embodiments

A number of embodiments have been described. Nevertheless, it will be understood that various modifications may be made without departing from the spirit and scope of the disclosure.

For example, while asthma treatments have been discussed above, the devices and methods disclosed herein may be used for the delivery of any type of vaporized medicine, and in any type of treatment involving such delivery. Other treatments include treatment of cystic fibrosis, croup, pneumonia, and other respiratory conditions. The devices and methods may also be used to deliver gases to patients, for example for substantially contact-free, hands-free oxygen delivery to a patient that cannot tolerate a mask or nasal cannula due to facial trauma or other issues.

Moreover, while various applications have been discussed above, the devices and methods may be used in many other applications where non-contact and/or hands-free delivery would be advantageous. For example, the devices may be used by paramedics or other EMS personnel in situations where the caregiver should remain seated, e.g., in a moving ambulance or other transport.

Also, in some devices the compressor and/or vaporizer may be integrally incorporated into the device, which may eliminate some tubes and connections.

Moreover, in various embodiments, not shown or described, various aspects may be modified to accommodate extended positioning of the device to reach more and additional degrees of freedom to adapt to different environments. The shape, size and configuration shown in the drawings and discussed above are meant only as an example and are not intended to be limiting.

Accordingly, other embodiments are within the scope of the following claims.

What is claimed is:

1. An apparatus comprising:
    a delivery tube;
    a positionable elongated member configured to support the delivery tube and maintain a distal end of the tube in a desired position, and to allow the position of the distal end of the tube to be adjusted by a user;
    a nebulizer cup disposed at a proximal end of the delivery tube, in fluid communication with the delivery tube and with a supply of compressed gas, the nebulizer cup being connected to the elongated member in a manner so that the nebulizer cup is supported in a substantially vertical position; and
    an attachment device configured to allow a proximal end of the elongated member to be supported in a fixed position.

2. The apparatus of claim 1 wherein the positionable elongated member comprises an articulated arm assembly.

3. The apparatus of claim 2 wherein the articulated arm assembly comprises two or more pivotably connected arm segments.

4. The apparatus of claim 1 wherein the positionable elongated member comprises a positionable tubular member.

5. The apparatus of claim 4 wherein the tubular member comprises gooseneck tubing, or continuously adjustable/flexible hollow tubing.

6. The apparatus of claim 1 further comprising a nozzle disposed at a distal end of the positionable elongated member.

7. The apparatus of claim 6 wherein the nozzle is configured to deliver a spray of vaporized nebulized medicament from the delivery tube.

8. The apparatus of claim 7 wherein the nozzle is configured to allow a user to adjust a spray pattern of the vaporized nebulized medicament.

9. The apparatus of claim 6 wherein the nozzle is attached to the distal end of the positionable elongated member by a ball joint that defines a lumen.

10. The apparatus of claim 2 wherein the positionable member includes at least three arm segments.

11. The apparatus of claim 1 wherein the attachment device comprises a base.

12. The apparatus of claim 11 wherein the base is configured to slip under a mattress.

13. The apparatus of claim 11 wherein the base is configured to rest flat on a floor or table.

14. The apparatus of claim 1 wherein the attachment device comprises a wall mount or clamp.

15. The apparatus of claim 1 wherein the proximal end is coupled to the attachment device so as to allow rotational or pivoting motion of the proximal end.

16. A method comprising:
    delivering a spray of nebulized vaporized medicine to the respiratory system of a patient, without the use of a mask, by positioning the distal end of a delivery tube adjacent the face of the patient using a positionable elongated member configured to support the delivery tube in a desired position relative to the patient, and delivering a compressed gas through a medicine cup containing the medicine, the medicine cup being mounted on the elongated member in a substantially vertical position, in fluid communication with a distal end of the delivery tube.

17. The method of claim 16 further comprising, prior to delivering, adding a supply of the medicine, in liquid form, to a nebulizer vaporizer mounted on the elongated member.

18. The method of claim 16 wherein the patient is lying down.

19. The method of claim 16 wherein the patient is an infant or child.

20. The method of claim 14 wherein the medicine comprises an asthma medicine.

21. The method of claim 16 wherein an adjustable nozzle is mounted at the distal end of the delivery tube and the method further comprises adjusting a spray pattern of the nebulized vaporized medicine using the adjustable nozzle.

22. The method of claim 16 further comprising, during delivery of the spray to the patient, delivering a spray of vaporized nebulized medicine to a second patient, without the use of a mask, by positioning the distal end of a second delivery tube adjacent the face of the second patient using a positionable elongated member configured to support the delivery tube in a desired position relative to the second patient.

* * * * *